United States Patent
Kosmecki et al.

(10) Patent No.: US 9,068,820 B2
(45) Date of Patent: Jun. 30, 2015

(54) METHOD AND DEVICE FOR CALIBRATING AN OPTICAL SYSTEM, DISTANCE DETERMINING DEVICE, AND OPTICAL SYSTEM

(75) Inventors: Bartosz Kosmecki, Berlin (DE); Andreas Reutter, Berlin (DE); Christopher Oezbek, Berlin (DE)

(73) Assignee: SCOPIS GMBH, Berlin (DE)

( * ) Notice: Subject to any disclaimer, the term of this patent is extended or adjusted under 35 U.S.C. 154(b) by 2 days.

(21) Appl. No.: 13/879,011

(22) PCT Filed: Oct. 17, 2011

(86) PCT No.: PCT/EP2011/068096
§ 371 (c)(1),
(2), (4) Date: Jun. 17, 2013

(87) PCT Pub. No.: WO2012/049326
PCT Pub. Date: Apr. 19, 2012

(65) Prior Publication Data
US 2013/0258353 A1    Oct. 3, 2013

(30) Foreign Application Priority Data
Oct. 15, 2010 (DE) .......................... 10 2010 042 540

(51) Int. Cl.
*G01B 11/14* (2006.01)
*A61B 1/00* (2006.01)
(Continued)

(52) U.S. Cl.
CPC ............ *G01B 11/14* (2013.01); *A61B 1/00057* (2013.01); *A61B 5/064* (2013.01);
(Continued)

(58) Field of Classification Search
CPC ...... G01B 11/27; G01B 7/105; G01B 11/275; G01B 21/042; G01B 2210/12; G01B 2210/306; G01B 3/00; G01B 5/0023; G01B 2203/021; G01B 2203/0292; G01N 27/4163; G01N 33/4925; G01N 3/00
See application file for complete search history.

(56) References Cited

U.S. PATENT DOCUMENTS

| 4,271,829 A | 6/1981 | Heckele |
| 4,958,932 A | 9/1990 | Kegelman et al. |

(Continued)

FOREIGN PATENT DOCUMENTS

| DE | 103 08 383 A1 | 9/2004 |
| DE | 10 2005 012 295 A1 | 9/2006 |

(Continued)

OTHER PUBLICATIONS

Khan M. "Computer Assisted Head and Neck, and ENT Surgery"nternational Journal of Computer Assisted Radiology and Surgery Jun. 2008, vol. 3, Issue 1 Supplement, pp. 79-85.

*Primary Examiner* — Michael P Stafira
(74) *Attorney, Agent, or Firm* — Maschoff Brennan (57) ABSTRACT

A method for calibrating a distance determining device for determining a distance between an optical system and an object. The method includes providing a detecting system having marking elements and a measuring camera. Using the distance determining device, a light structure is projected onto a carrier that provides a calibration pattern. The measuring camera detects the marking elements or the calibration pattern to determine the spatial position of the optical system. Coordinates of a calibration pattern in a coordinate system associated with the measuring camera are determined. An image of the calibration pattern and the light structure is created using a camera of the optical system. Coordinates of an image of a calibration pattern and the light structure in a coordinate system associated with the camera image plane are determined. The distance determining device is calibrated using the determined coordinates and the determined spatial position of the optical system.

18 Claims, 9 Drawing Sheets

(51) Int. Cl.
- *A61B 5/06* (2006.01)
- *G01B 21/04* (2006.01)
- *G01S 5/16* (2006.01)
- *G01S 7/497* (2006.01)
- *A61B 19/00* (2006.01)
- *A61B 17/00* (2006.01)

(52) U.S. Cl.
CPC ............ *A61B 5/065* (2013.01); *A61B 19/5212* (2013.01); *A61B 19/5244* (2013.01); *A61B 2017/00725* (2013.01); *A61B 2019/5255* (2013.01); *G01B 21/042* (2013.01); *G01S 5/163* (2013.01); *G01S 7/497* (2013.01)

(56) References Cited

U.S. PATENT DOCUMENTS

| | | | |
|---|---|---|---|
| 4,980,763 A | 12/1990 | Lia | |
| 5,987,960 A | 11/1999 | Messner et al. | |
| 6,081,336 A | 6/2000 | Messner et al. | |
| 6,135,946 A * | 10/2000 | Konen et al. | 600/117 |
| 6,511,418 B2 | 1/2003 | Shahidi et al. | |
| 6,517,478 B2 | 2/2003 | Khadem | |
| 7,486,805 B2 | 2/2009 | Krattiger | |
| 7,688,998 B2 | 3/2010 | Tuma et al. | |
| 2003/0031349 A1 | 2/2003 | Giorgi et al. | |
| 2007/0021738 A1 | 1/2007 | Hasser et al. | |
| 2007/0168146 A1* | 7/2007 | Horijon et al. | 702/94 |

FOREIGN PATENT DOCUMENTS

| | | |
|---|---|---|
| DE | 10 2005 047 481 A1 | 4/2007 |
| EP | 0 4033 399 A2 | 12/1990 |
| EP | 0 904 735 A2 | 3/1999 |
| EP | 0 905 538 A2 | 3/1999 |
| EP | 1 279 376 A2 | 10/2001 |
| EP | 1 563 799 A1 | 8/2005 |
| WO | 01/35849 A1 | 5/2001 |
| WO | 01/74266 A1 | 10/2001 |
| WO | 2007/068017 A2 | 6/2007 |

* cited by examiner

METHOD AND DEVICE FOR CALIBRATING AN OPTICAL SYSTEM, DISTANCE DETERMINING DEVICE, AND OPTICAL SYSTEM

CROSS-REFERENCE TO A RELATED APPLICATION

This application is a National Phase Patent Application of International Patent Application Number PCT/EP2011/068096, filed on Oct. 17, 2011, which claims priority of German Patent Application Number 10 2010 042 540.0, filed on Oct. 15, 2010.

The invention relates to a method for calibrating an optical system, a calibrating device, a distance determining device and an optical system.

Optical systems with a distance determining device are known from the prior art, which can determine distances, in particular distances of the optical system to an object based on the principle of triangulation by means of collimated radiation (in particular laser radiation). If also the spatial position of the optical system is determined additionally to the distance, the spatial position of the area of the object, which is stricken by the collimated radiation, can be determined.

SUMMARY

The object to be solved by the present invention is to provide a method and a device which allows for a preferably simple and fast calibration of a distance determining device of an optical system. A further object of the invention is to provide the possibility to be able to determine the distance and/or the spatial position of an optical system as exact as possible and in a preferably simple manner.

According to an exemplary embodiment of the invention a method for calibrating a distance determining device for determining a distance or position vector between an optical system and an object is provided comprising the steps:

a) providing a detecting system, which comprises a plurality of marking elements and a measuring camera for detecting the spatial position of the marking elements;

b) arranging the marking elements on the optical system and/or the distance determining device;

c) providing a carrier to which a calibration pattern is connected and/or which forms a calibration pattern;

d) projecting a light structure onto the carrier by means of the distance determining device;

e) (in particular simultaneous) detecting the marking elements, the calibration pattern and/or carrier marking elements arranged on the carrier by means of the measuring camera;

f) determining the spatial position of the marking elements and thus of the optical system using data of the measuring camera;

g) determining coordinates of the calibration pattern in a first coordinate system associated with the measuring camera using data of the measuring camera;

h) creating an image of the calibration pattern and the light structure by means of a camera of the optical system;

i) determining coordinates of the image of the calibration pattern and the light structure in a second coordinate system associated with the image plane of the camera; and j) calibrating the distance determining device using the determined coordinates and the determined spatial position of the optical system.

The distance determining device is arranged in an in particular preset (known) spatial relation to the optical system, for example said device is rigidly connected to the optical system. The detecting system (which is for instance designed in form of a clinical measuring system, in particular a clinical navigation system or as part of a clinical navigation system) is a detection system which allows determining the position of a (in particular medical) instrument, for instance of an optical system (e.g. an endoscope), using the marking elements and the measuring camera. Thereby, the measuring camera of the detection system is based in particular on the principle of a stereo camera, that means said camera comprises for instance two sensor elements (in particular CCD ships) distanced to each other, which receive light from an object (in particular from a marking element of the detection system) at different angles and at different time points such that the spatial position of the object can be reconstructed form the data of the sensor elements.

Active (self luminating) elements, as for instance LEDs, or passive (non-self luminating) elements, as for instance reflecting spheres, films or specific patterns (flat target marks, laser gravures or natural patterns like corners and edges) can be used as marking elements. When using passive marking elements it is in particular possible that the measuring camera emits light impulses, in particular in the infrared wavelength area, which are reflected by the marking elements and again detected by the measuring camera.

Thus, the spatial positions of the marking elements, i.e. their spatial coordinates in a preset coordinate system associated to the measuring camera, can be determined. If the relative position of the marking elements in respect to the system on which said elements are attached is known, the position of the system can be concluded from the spatial positions of the marking elements, wherein the term "position" means also the orientation of the system.

The calibration pattern arranged on the carrier consists at least partially of marking elements, which can be detected by the measuring camera such that by detecting the calibration pattern by the measuring camera the spatial position of the calibration pattern or at least of parts of the calibration pattern can directly be determined. According to an embodiment of the invention marking elements detectable by the measuring camera are arranged (rigid) alternatively or additionally on the carrier (carrier marking elements) such that in case of a known position of the calibration pattern relative to the marking elements the spatial position (spatial coordinates) thereof in the coordinate system of the measuring camera can be determined via the position of the marking elements.

By arranging marking elements (which are e.g. designed similar or identical to the marking elements arranged on the optical system) on the carrier it is in particular possible to provide in principle any calibration pattern which has to be detectable by the camera associated to the distance determining device (which is in particular part of the optical system, at which the distance determining device is arranged) but not necessarily by the measuring camera. For example, at least three marking elements are arranged on the carrier, of which at least three are detected by the camera associated to the distance monitoring device.

The measuring camera of the detection system is in particular arranged and aligned such that said camera does not only detect marking elements attached to the optical system to be calibrated, but simultaneously also the calibration pattern and/or the above-mentioned carrier marking elements attached to the carrier. In analogy to determining the positions of the marking elements arranged on the optical system thus the spatial coordinates of the calibration pattern can also be simultaneously determined using the measuring camera. For example, the calibration pattern comprises a grid of points which is detected by the measuring camera. Thus, the spatial position of the optical system and also the coordinates of the calibration pattern (or at least of sub-areas of the calibration pattern) are determined via the measuring camera (in particular at one and the same time point).

Measuring cameras (which are for instance part of a clinical measuring system, specifically of a clinical navigation system) for detecting the position of the marking elements are known as such so that they have not to be further explained at this point. An example of a commercially available measuring camera (and in principle suitable for conducting the method according to the invention) is the system "CamBar B2" of the AXIOS 3D Services GmbH. The invention is however of course not restricted to the use of a specific kind or a specific type of measuring camera.

Using the optical system, with which a distance determining device to be calibrated is associated (and is for instance attached), an image of a calibration pattern and the projected light structure is taken (in particular simultaneously to the determination of the spatial position of the calibration pattern and the optical system by means of the measuring camera of the detection system), e.g. the optical system comprises a CCD camera, by which an image (in particular in form of a video image) of the calibrating structure and the light structure to be generated is taken.

The distance determining device of the optical system to be calibrated, by which in particular a distance between a section of the optical system to be turned to the object to be imaged and the object can be determined, comprises e.g. means (in particular in form of a laser) for projecting the light structure onto the object to be imaged and interacts with an image optic and a camera of the optical system.

The means for projecting are arranged relative to an image optic of the optical system (e.g. in form of an endoscope) for imaging an object into the image plane of a camera of the optical system (which is the camera "associated to the distance determining device") in particular such that between the light bundle emitted by the means for projecting and the reflected light bundle, which falls from the object into the image optic of the optical system, an angle (for instance 30° C.) exists, such that the position of the image of the light pattern generated on the object in the image plane of a camera depends on the distance of the object to the optical system. It is in particular also conceivable that by means of the distance determining device, a position vector between a point of the optical system and a point of the light structure projected by the distance determining device is determined, i.e. not only the distance, but also the orientation of a connecting line between these points is determined.

The optical system can be also a microscope, wherein the distance determining device comprises in particular a laser triangulation sensor, which generates a light structure, which is projected for calibration in the field of vision of the microscope onto the object to be imaged. For this purpose marking elements are arranged in particular on the laser triangulation sensor via which the spatial position thereof can be detected. Furthermore, a calibration pattern is provided on a carrier, wherein the spatial position thereof can be also determined via carrier marking elements. The laser triangulation sensor is connected rigidly to the microscope such that a light structure projected therefrom and the calibration pattern can be imaged by a camera of the microscope. The calibration occurs then by means of this image and the determined positions of the calibration pattern and the laser triangulation sensor.

According to the method of the invention coordinates of a calibration pattern are determined on one hand in a first (in principle any) coordinate system of the measuring camera and on the other hand coordinates of the image of a calibration pattern and the light structure are determined in a second coordinate system. The second coordinate system is e.g. a 2D coordinate system, which extends along the image plane of a camera of the optical system to be calibrated. For example, a CCD chip is located in the image plane of the optical system, whereby the origin of the second coordinate system is e.g. in the plane of the CCD chip. It is also conceivable to specify a pair of pixel numbers as second coordinates, which characterize the light sensitive pixels of the CCD chips.

However, it is also possible that the first coordinate system is generated by the calibration pattern and the coordinates of the projected light structure (e.g. a light point or multiple light points) are determined relative to these coordinates. In analogy, the second coordinate system can be defined by the image of the calibration pattern in the image plane of the camera, whereby the coordinates of the image of the light structure is specified relative to these coordinates. For example, the calibration pattern consists of a grid of points (or other structures) with a constant distance to each other, wherein the points of the grid form the first coordinate system.

The determination of the coordinates of the projected light structure occurs now relative to these coordinates, wherein the determination of the coordinates occurs in particular by determining the distance to the nearest points of the grid. The determination of the coordinates of the image of the light structure occurs in analogy, whereby the image of the grid of points defines the second coordinate system. The grid of points can be distorted in particular by image errors (distortions) of the image optic of the optical system such that the image of the grid of points generates a curve linear coordinate system. It is to be pointed out that the calibration pattern does not have to be necessarily realized in form of a regular grid of points. It can rather comprise also an irregular pattern of light structures (e.g. points) which defines the first coordinate system.

It is additionally pointed out that the term "calibration" is to be understood in particular as an adjusting or calibrating according to the definition of the norm DIN 1319.

A "calibration" is defined in the norm DIN 1319 as follows: "determining the relation between measuring value or expected value of the output value and the assigned true or right value of the measuring value present as input value for a measuring device considered at said conditions. During calibration no intervention occurs, which changes the measuring device.

The term "adjustment" is defined in the norm DIN 1319 as follows: "setting or matching a medium device in order to remove systematic measuring deviations as far as required for the intended application. Adjustment requires an intervention which changes the measuring device permanently".

According to a further exemplary embodiment of the invention, the optical system is in a first position during the steps d) to i) and is brought from the first into a second position after conducting the steps d) to i), wherein the optical system has in the second position, for instance, another distance to the carrier with the calibration pattern than in the first position. The steps d) to i) are carried out again for the second position. First coordinates of the calibration pattern in the first coordinate system and second coordinates of the image of the calibration pattern and the light structure in the second coordinate system are determined for the first and the second position, respectively, wherein the optical system is calibrated by means of these coordinates considering the respective determined spatial position of the optical system. In the following the coordinates (of the calibration pattern and/or the light structure) in the first coordinate system (i.e., the respective spatial coordinates) are to be understood as the "first coordinates" and the coordinates in the second coordinate system (i.e. the image coordinates) are to be understood as "second coordinates", respectively.

In other words, the optical system to be calibrated is moved at first into the first position and coordinates of the calibration pattern and coordinates of the image of the calibration pattern and the light structure are determined in this position. Subsequently, the optical system is moved from the first position into a second position. An image of the calibration pattern and the coordinates of the calibration pattern and the coordinates of the image of the calibration pattern and the light structure are determined as in the first position by means of the optical system located in the second position. Furthermore, also the coordinates of the light structure in the first spatial coordinate system are in particular determined in each case, whereby this is done by means of the first and second coordinates of the calibration pattern and the second coordinates of the light structure.

Since the position of the carrier with the calibration pattern can be determined via the marking elements attached to the carrier, also the spatial (first) coordinates of e.g. points of the calibration pattern can be determined, as mentioned. Furthermore, the image coordinates (the second coordinates) of the points (or also of non-punctiform structures) of the calibration pattern are determined such that an assignment of the image coordinates of the points of the calibration pattern to the spatial coordinates of the points of the calibration pattern can occur. Since the image coordinates of the light structure are also known, the position thereof in the second coordinate system relative to the position of the points of the calibration pattern can be determined. Thus, it is possible to determine the spatial coordinates of the light structure by interpolation of the spatial coordinates of the points of the calibration pattern. For example, the structures (e.g. points) of the calibration pattern form a grid, wherein e.g. the distance of the image of the light structure to the neighbouring images of the structures of the calibration pattern is determined. The calibration pattern structures corresponding to the neighbouring images of the calibration pattern structures (arranged on the carrier) are identified and the spatial (first) coordinates thereof are determined. Subsequently, it is interpolated between these first coordinates of the calibration pattern structure and based on this interpolation and the distances of the image of the light structure from the images of the neighbouring calibration pattern structures the spatial coordinates of the light structure are determined.

In general, a proximity image adapted to the first and second coordinates of the calibration pattern can be determined for determining the spatial coordinates of the light structure by which first coordinates (image coordinates) can be imaged in second coordinates (spatial coordinates). The spatial coordinates of the light structure are then determined in addition to the image coordinates of the light structure by means of this proximity image.

Furthermore, it is conceivable that for the different positions of the optical system the first coordinates of the light structure are illustrated by a first proximity function (for instance in form of a first polynomial) and/or the second coordinates of the light structure are illustrated by the second proximity function (for instance in form of a second polynomial), wherein the proximity functions image e.g. a distance between the projected light structure and the optical system onto the first or second coordinates. Furthermore, a transfer function for imaging the first proximity function on the second proximity function can be determined, wherein by means of said transfer function the spatial coordinates of the associated light structure projected onto the carrier can be determined from the second coordinates of the light structure. According to a further modification of the invention, the first proximity function is determined and the optical system is brought into at least one further position, wherein the calibration according to step j) for the at least one further position comprises the following steps:

i. determining the second coordinates of the light structure,
    ii. determining a line ("visible beam line") in the first coordinate system, which continues through the position of the light structure in the image plane of the optical system and through an optical centre of the optical system, and
    iii. determining the first coordinates of the light structure projected onto the carrier by determining the coordinates of the intersection of the lines by means of the first proximity function.

The first proximity function can be for instance illustrated as a line ("light line" which continues through the first coordinates of the light structure determined for the different positions of the optical system) and the coordinates of the light structure projected on the carrier in the first coordinate system are determined by determining the coordinates of the intersection of the line determined according to step ii) with the line illustrating the first proximity function or by determining the coordinates of a point (for instance a centre point) of a common perpendicular relative to the two lines. The visible beam line can be determined in particular also in dependency on further optical properties of the optical system, for instance depending on its distortion properties.

The coordinates determined for the first position as well as also for the second position of the optical system are used finally for calibrating the distance determining device. The optical system can be brought of course in more than two positions, wherein for each of these positions the coordinates of the calibration pattern and the coordinates of the image and the light structure are determined and the calibration is carried out by using all of these coordinates as determined.

The optical system at which the distance determining device is attached to can for instance be hold by hand during the calibration process and thus can for instance also be moved from one to position into another. The optical system can of course also be arranged in a holder and can for instance also be moved in the holder relative to the calibration pattern (or to the carrier on which the calibration pattern is formed).

The optical system is positioned during the calibration process e.g. in different distances (e.g. between 0.5 and 20 mm and e.g. in 0.1 mm increments) to the carrier with the calibration pattern, whereby it is moved e.g. along a line (for instance moved along a guide). In addition, the optical system can also be aligned at different angles to the carrier, whereby e.g. for each angle different distances of the optical system to the carrier are passed through. It is also conceivable that in addition multiple carriers with different surface properties are used.

The coordinates determined by means of the measuring camera are for instance, as already mentioned above, spatial coordinates, i.e. they comprise three coordinate values, respectively, while the coordinates of the image of the calibration pattern are e.g. plane coordinates, which refer to the image plane of the camera of the optical system and comprise only two coordinate values, respectively. Since multiple positions of the optical system relative to the carrier with the calibration pattern can be measured, a plurality of 3D-2D coordinates pairs result, which can be used for calibrating the optical system.

The calibration of the optical system by using the determined coordinates can also e.g. consist in creating a calibration table (look-up table), in which the coordinates of the projected light structure determined for each position of the optical system relative to the calibration pattern are contrasted with the coordinates of the image of the light structure. Such a calibration table contains e.g. the spatial coordinates (in the coordinate system of the measuring camera) of the light structure generated by the distance determining device for each measured position of the optical system to which in each case the coordinates (in the coordinate system of the image plane of the camera of the optical system) of the image of the light structure are assigned.

If a calibration table is for instance generated, in which the first coordinates of the light structure determined for the first and the second position as well as the first coordinates of the light structure projected onto the carrier and determined for the at least one further position of the optical system as described above are contrasted with to the respective second coordinates of the light structure.

With the assistance of such a calibration table a spatial position of the light structure is thus assigned to a position of the light structure (e.g. in form of a singular light spot) generated by the distance determining device and imaged by the optical system, with which the distance determining device is associated.

The calibration table can contain additionally also information in respect to the angles between an optical axis of the optical system and the carrier with the calibration pattern. This angle is determined in particular by using the spatial position of the optical system determined with the assistance of the marking elements arranged on the optical system. Furthermore, the calibration table can also contain information about the respective spatial position of the optical system, e.g. the position and/or orientation thereof such that the calibration can be used for in principle any orientation and position of the optical system relative to the distance determining device. Positions and orientations can be excluded in which the light beam of the distance determining device with the optical system is always imaged on the same point of the two-coordinate system.

It is furthermore conceivable that with the assistance of the determined (first and second) coordinates of the calibration pattern and the determined spatial position of the optical system a distance or a position vector between the carrier and the calibration pattern and the optical system is determined and this distance or position vector is brought into relation to the position of the image of the light structure in the image plane of the optical system (for instance also with a calibration table).

It is also conceivable that in each case for the first and the second position (or also for further positions) of the optical system a position vector between a point of the light structure projected onto the carrier and a point of the optical system is determined and calibrating according to step j) comprises the assignment of this position vector to the determined second coordinates of the light structure (e.g. in the calibration table). For this reason, the coordinates the point of the light structure projected onto the carrier are determined in particular as described above, i.e. by using the first and second coordinates of the calibration structure and the second coordinates of the light structure.

For this purpose, for instance, the relative position of the marking elements arranged on the optical system and a side of the optical system to be turned to the object to be imaged is known. The optical system is for instance an endoscope, which comprises a tip, which is to be turned to the object to be imaged and the position thereof relative to the marking elements arranged on the endoscope is known. Therefore, the position of the endoscope tip can be concluded from determining the position of the marking elements and a distance between the endoscope tip and the projected light structure can be determined by means of the determined spatial coordinates of the light structure. It is also possible that the amount and/or the direction of a position vector between the position of the endoscope tip (or another reference point of the optical system) and the projected light structure are brought into relation to the coordinates of the image of the light structure.

The invention relates also to a calibration device for calibrating a distance determining device for determining a position vector between a known point of an optical system and a marked point of an object, in particular for carrying out a method as described above, comprising
  a) a carrier to which a calibration pattern is connected and/or which forms a calibration pattern;
  b) a detection system, which comprises a plurality of marking elements arranged on the optical system and/or the distance determining device and a measuring camera for detecting the spatial position of the marking elements, of the calibration pattern and/or of carrier marking elements arranged on the carrier;
  c) position determining means for determining the spatial position of the optical system by means of data of the measuring camera;
  d) coordinate determining means for determining coordinates of the calibration pattern in a first coordinate system associated with the measuring camera, of coordinates of an image of the calibration pattern and the light structure in a second coordinate system associated with the image plane of a camera of the optical system; and
  e) calibration means for calibrating the distance determining device by means of the determined coordinates and the determined spatial position of the optical system.

The position determining means are in particular part of the (in particular clinical) detection system and are realized for instance in way of a software or a correspondingly programmed electronic component. The "detection system" is formed as already explained above in particular in form of a clinical measuring system, in particular in form of a clinical navigation system or in form of a part of a clinical measuring system. The coordinates determining means and/or calibration means are also designed in particular in form of a software or a accordingly programmed electronic component.

The calibration device comprises for instance means (in particular a laser) for generating a light pattern to be arranged in a distance to the calibrating optical system, as already described above.

The calibration pattern can be furthermore glued on to the carrier, printed and/or engraved into the carrier. It is also possible that the carrier comprises connecting means for connecting to the optical system. The connecting means are in particular designed such that they allow for a relative movement between the carrier and the optical system such that different distances between the carrier and the optical system can be adjusted. The connecting means comprise for instance a guidance (e.g. a rail) via which the optical system can be moved linear relative to the carrier.

In a further aspect the invention comprises a distance determining device for an optical system, in particular in form of an endoscope, for determining a distance between the optical system and an object comprising a first channel continuing in direction of an optical axis of the optical system in which a section of a light conducting fibre is guided which serves for conducting and emitting light in direction of the object; and a second channel in which a further section of the light conducting fibre is guided and which continues such that the further section of the light conducting fibre is bent in direction to the first channel.

The light conducting fibre (in particular in form of a glass fibre) is coupled for instance to a laser of the distance determining device and conducts light of the laser to an emitting side of the optical system. The channel in which the light conducting fibre is guided is in particular a longitudinal hollow body e.g. in form of a (for instance metallic) tube.

The distance determining device comprises for instance a base body in which a receptacle for a light guiding shaft of the optical system continuing along the optical axis of the optical system. Furthermore, a notch can be provided in the base body, which forms the second channel for guiding the light conducting fibre.

The second channel comprises for instance a first, second and third section, wherein the second section is connected with one of the ends thereof via a first curvature to the first section and with the other end thereof via a second curvature to the third section. The second channel allows thus a reflection of the light conducting fibre at preferably low radiation losses. The curvature radius of the first and (or the second curvature) is for instance at least 5 mm.

The invention relates also to an optical system (in particular an endoscope or microscope) with the distance determining device according to the invention.

In a further aspect the invention relates to an optical system comprising a plurality of marking elements for determining the spatial position of the optical system; and connecting means via which the marking elements are pivotably connected to the optical system.

The marking elements, which are e.g. designed as above described, are for instance arranged in a common holder, which is pivotably connected via the connecting means to the optical system.

According to an embodiment of the optical system the marking elements can be pivoted via the connecting means about an axis, which continues parallel to an optical axis of the optical system. The optical system can be for instance (e.g. a rigid) endoscope, wherein the optical axis of the endoscope is assigned in particular by the optical axis of the optical image system of the endoscope.

A distance determining device as described above can be furthermore arranged on the optical system of the optical system.

BRIEF DESCRIPTION OF THE DRAWINGS

The invention is explained in more detail in the following by the means of examples with reference to the Figures.

FIGS. 11, 11B show a further perspective view of the endoscope of FIGS. 7 and 8 in an assembled status or in explosive view

DETAILED DESCRIPTION

Figure 1:
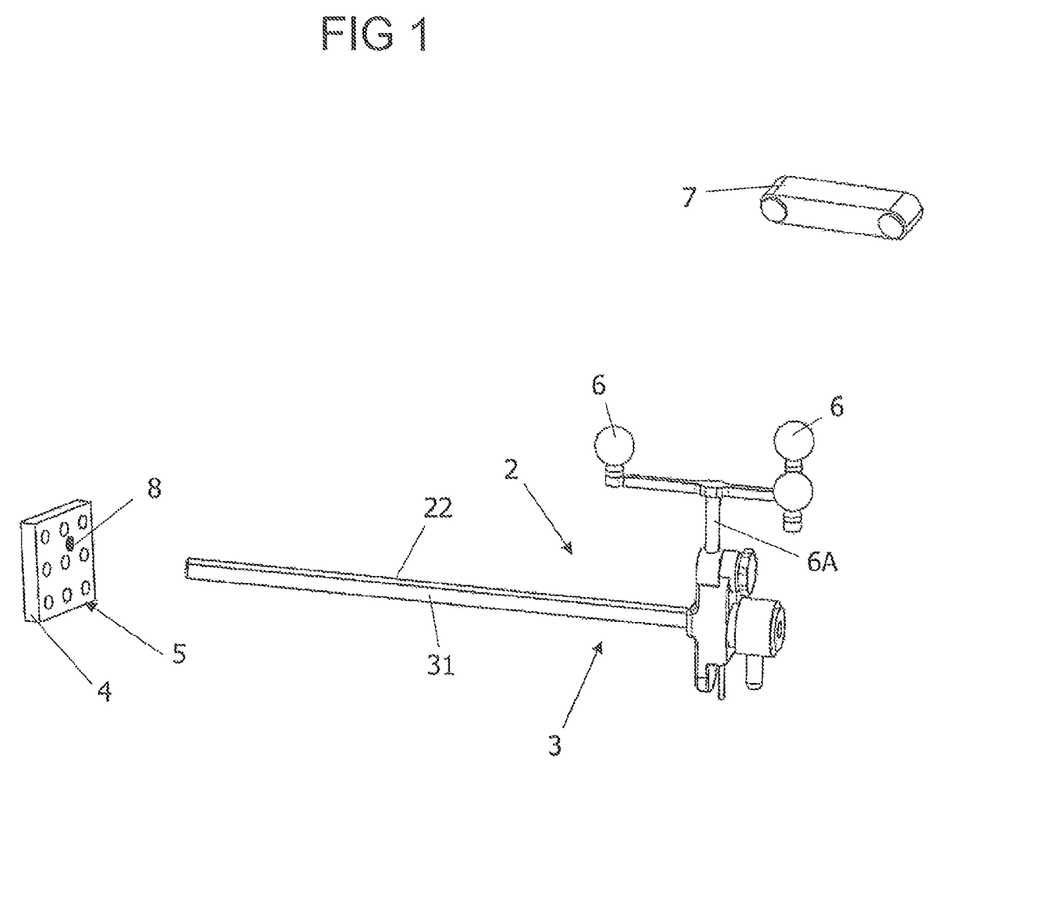
FIG. 1 shows a calibration device according to a first embodiment of the invention.

The calibration device illustrated in FIG. 1 serves for calibrating a distance determining device 2 of an optical system in form of an endoscope 3. The distance determining device 2 comprises a laser (not shown) the light thereof is guided via a light conducting fibre 22 extending with the subsection along an endoscope shaft 31 to the tip of the endoscope and is projected onto the object to be examined by the means of the endoscope. The light spot generated by the distance determining device on the object is imaged via the image optic and a camera (not shown) of the endoscope, whereby the distance between the endoscope tip and the object can be determined from the position of the light spot in the image plane of the camera.

The calibration device 1 comprises a carrier 4 to which a calibration pattern 5 is connected and which is positioned such that by using the distance determining device a light spot 8 is projected on the carrier 4 and by using the camera of the endoscope 3 an image of the calibration pattern 5 and the light spot 8 can be generated. The calibration pattern 5 consists of a plurality of grid-like calibration points arranged on the carrier, which are e.g. printed or glued onto the carrier 4.

The calibration device 1 comprises furthermore a detection system which comprises multiple marking elements in form of reflective marking spheres 6. The marking spheres 6 are connected via a common holder 6A to the endoscope 3. The detection device comprises furthermore a measuring camera in form of a stereo camera 7 which is arranged such that said camera can detect simultaneously the marking spheres 6 and the calibration pattern 5. The calibration device 1 comprises also position determining means (not shown), which determine the spatial position (i.e. the coordinates of one or multiple reference points of the endoscope and the orientation thereof in space) from the data of the measuring camera 7. The position determining means are designed in particular in form of a correspondingly programmed computer.

The calibration device comprises furthermore coordinate determining means, which can be designed e.g. also in form of a computer program, which determine by means of the data of the measuring camera 7 first coordinates in form of spatial coordinates of the calibration pattern 5.

The coordinate determining means determine furthermore also coordinates of the image of the calibration pattern 5 generated by the camera of the endoscope and the light spot 8 in a second coordinate system associated to the image plane of the camera of the optical system. Calibration means (which are also in particular designed as computer programs) of the calibration device calibrate subsequently the distance determining device 2 of the endoscope by means of the determined (first and second) coordinates as well as the determined spatial position of the optical system.

The calibration of the distance determining device 2 with assistance of the calibration device of FIG. 1 occurs such that the endoscope 3 is brought into different positions (in particular distances) relative to the carrier 4 (i.e. to the calibration pattern 5) and in each case the coordinates of the calibration pattern 5 are determined in space. In addition, an image of the calibration pattern 5 and the light spot 8 is generated by means of the camera of the endoscope 3 and the coordinates of the calibration pattern and the light spot in the image plane of the camera are determined by means of the coordinate determining means. Moreover, the spatial coordinates of the light spot 8 are determined by means of the known spatial coordinates of the calibration pattern and the coordinates of the image of the calibration pattern and the image of the light spot.

According to the embodiment of FIG. 1, the calibration pattern 5 consists as mentioned of a grid of calibration points wherein in each case the coordinates of the singular calibration points are determined. The calibration means generate then a calibration table in which for instance for each distance of the endoscope 3 from the calibration pattern 5 the spatial coordinates of the light spot 8 on the carrier is contrasted with the coordinates of the image of the light spot 8. Thus, after calibrating the distance determining device (i.e. after finishing the calibration table) a spatial position of the light spot projected on an object can be assigned to a position of the light spot in the image plane of the camera. Thereby it may occur that the position of the image of the light spot is between light spot positions contained in the calibration table such that the assigned spatial position of the light spot on the object has to be carried out by interpolation of the values included in the calibration table.

It is also conceivable that during the calibration process a distance of a reference point (e.g. the tip of the shaft 31 of the endoscope 3) and the carrier is assigned to a position of the image of the light spot instead of the spatial position of the light spot 8 projected onto the carrier. The distance of a reference point of the endoscope to the object can be then determined after calibration of the distance determining device from the position of the light spot in the image plane, wherein the distance again optionally has to be determined by interpolation of values included in the calibration table, which are adjacent to the actual position of the light spot in the image plane.

It is also possible that the spatial positions of the light spot 8 projected onto the carrier are included in the calibration table; these however are not specified absolutely but relative to a reference point of the endoscope (as already mentioned above e.g in form of a tip of the endoscope). The actual position of the light spot in space relative to the reference point can then be determined after calibration of the distance determining device from the position of the image of the light spot generated by the distance determining device on the object to be examined in the image plane of the camera and after determining the spatial position of the endoscope (of another optical system).

Figure 2:
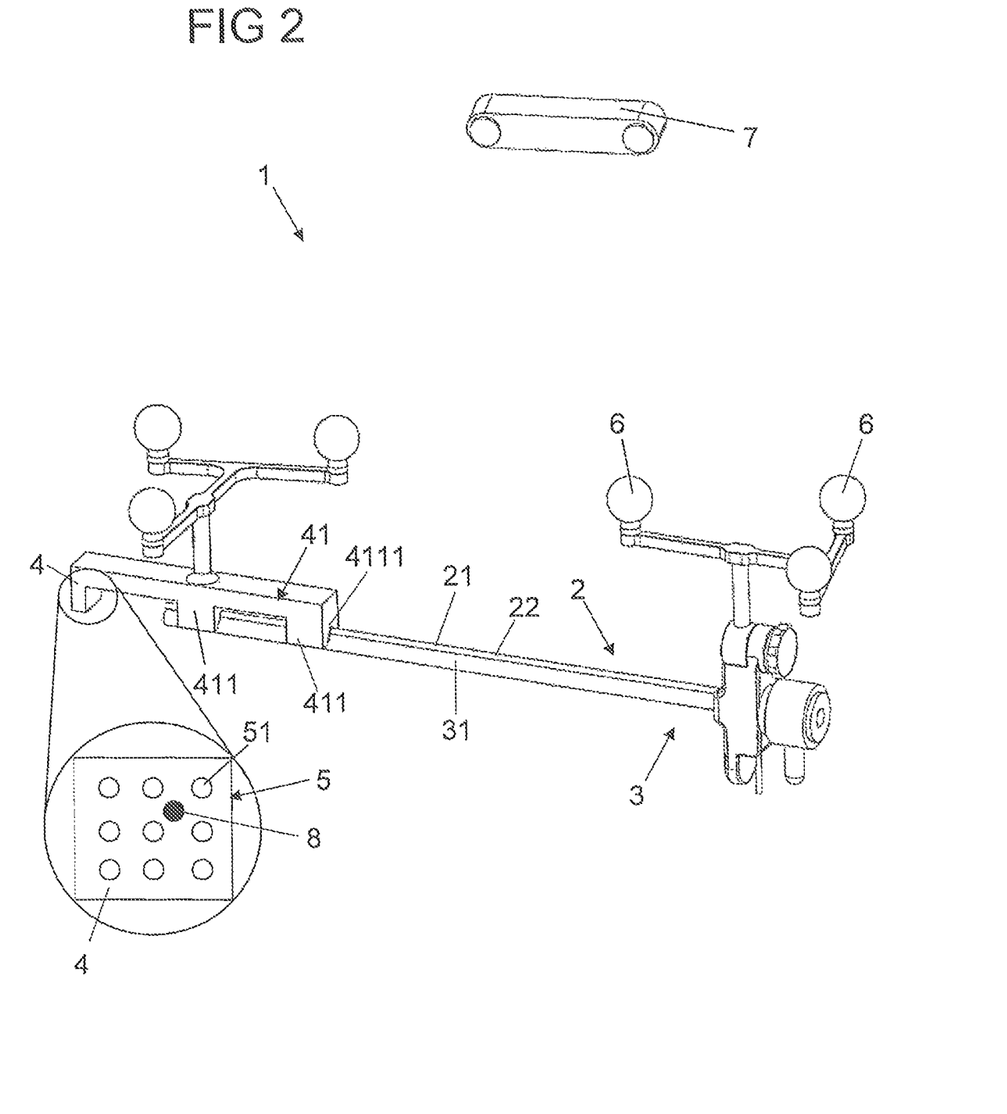
FIG. 2 shows a calibration device according to a second embodiment of the invention.

FIG. 2 is a further embodiment of the calibration device according to the invention, which comprises a stereo camera 7 and as well a calibration pattern 5 consisting of multiple grid-like arranged calibration points 51 as in the calibration device of FIG. 1. Likewise in FIG. 1 the calibration pattern is connected to a carrier 4.

In contrast to FIG. 1, the carrier 4 with the calibration pattern 5 is however not arranged separately to the distance determining device 2 of the endoscope 3, but connected via connecting means in form of a guidance 41, which is movably coupled to the shaft 31 of the endoscope 3. The carrier 4 is formed in particular in one piece with the guidance 41, wherein the guidance 41 comprises two brackets 411, in which in each case a guidance groove 4111 is formed which is adapted to the outer dimensions of the endoscope shaft 31 and to a tube 21 continuing along the endoscope shaft 31, in which the light conducting fibre 22 of the distance determining device 2 extends.

The guidance 41 is thus attached to the endoscope shaft 31 and can be moved during the calibration process along the optical axis of the endoscope, which is determined by the course of the shaft 31 (in which the image optic of the endoscope is arranged) such that different distances between the carrier 4 to the calibration pattern 5 and the tip of the endoscope shaft 31 can be adjusted. Accordingly, different distances are adjusted during the calibration of the distance determining device 2 by moving the guidance 41 on the endoscope shaft 31 and as explained above the coordinates of the calibration point 51 and the coordinates of the respective images of the calibration points and of the light spot 8 projected by the distance determining device 2 in the image plane of the camera are determined, respectively, and a calibration table is generated.

Figure 3:
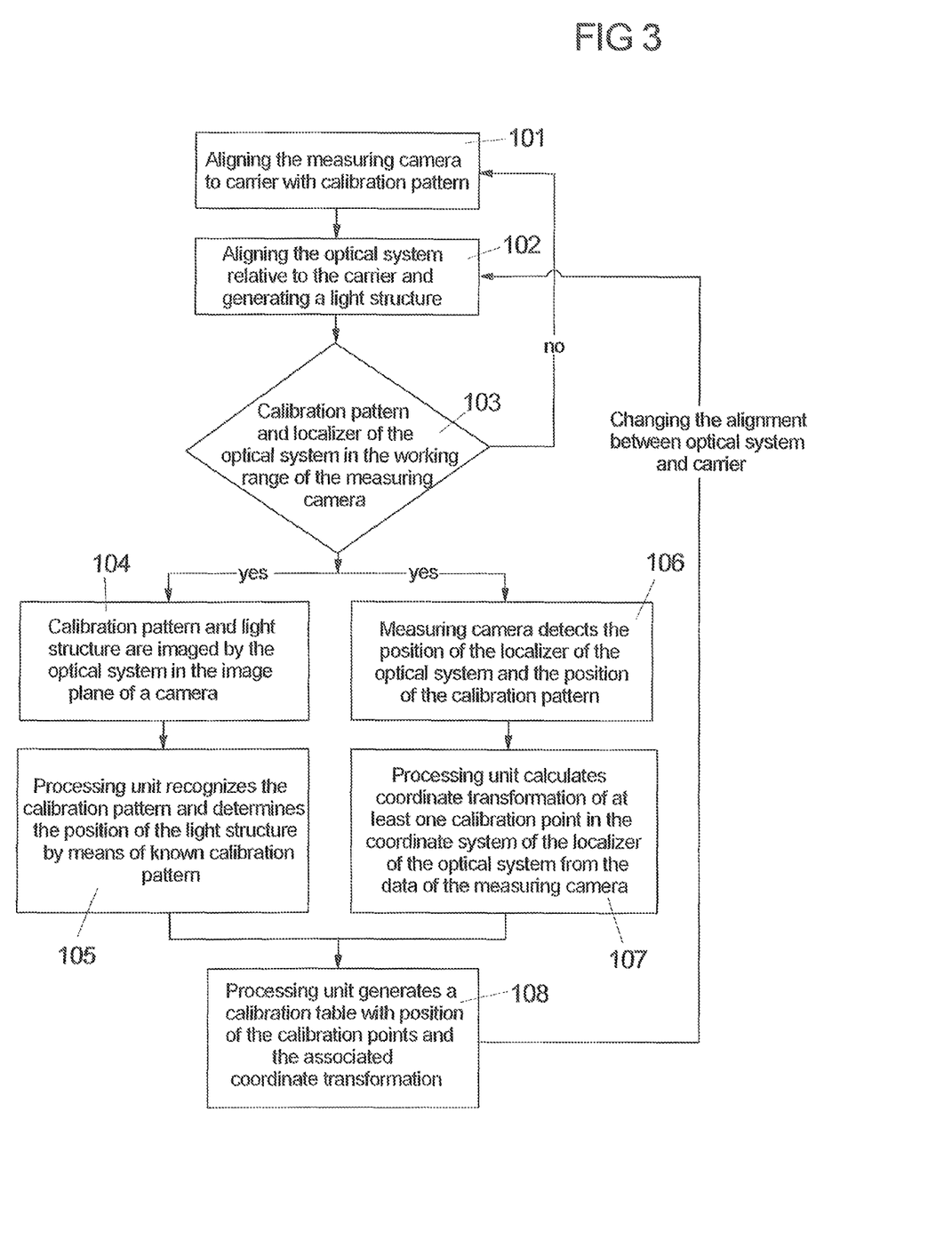
FIG. 3 shows a flow diagram for explaining the method according to the invention.

FIG. 3 is a flow diagram for illustrating the calibration method according to the invention, which is in particular carried out by using a calibration device of FIG. 1 or 2.

The optical system is positioned relative to the carrier after aligning a measuring camera on the carrier with the calibration pattern such that a light structure is generated on the carrier by means of the distance determining device of the optical system and the carrier, as well as marking elements arranged on the optical system can be detected by the measuring camera (steps 101, 102). For example, the optical system is aligned such that the optical axis thereof (e.g. the axis of the endoscope shaft if the optical system is an endoscope) is oriented at least approximately vertical to the carrier.

Subsequently, it is tested if the calibration pattern and the marking elements of the optical system fixed to the optical system are in viewing range of the measuring camera of the detection system (step 103). If this is the case, on the one hand the calibration pattern and the light structure are determined according to the steps 104, 105 by a camera of the optical system (e.g. on a CCD-chip of the camera) and the (second) coordinates of the imaged calibration pattern and the light structure.

On the other hand, the position of the marking elements ("localizer") and the position of the calibration pattern in the first coordinates system are detected by the measuring camera (step 106), wherein the measuring camera detects the position of the calibration pattern either directly or via a further localizer ("carrier marking elements") on the carrier of the calibration pattern.

After determining the (first and second) coordinates an entry in the calibration table is created, which contrasts the determined coordinates (steps 107, 108). Subsequently, the optical system is moved into another position and the steps 104 to 108 are repeated.

Figure 4:
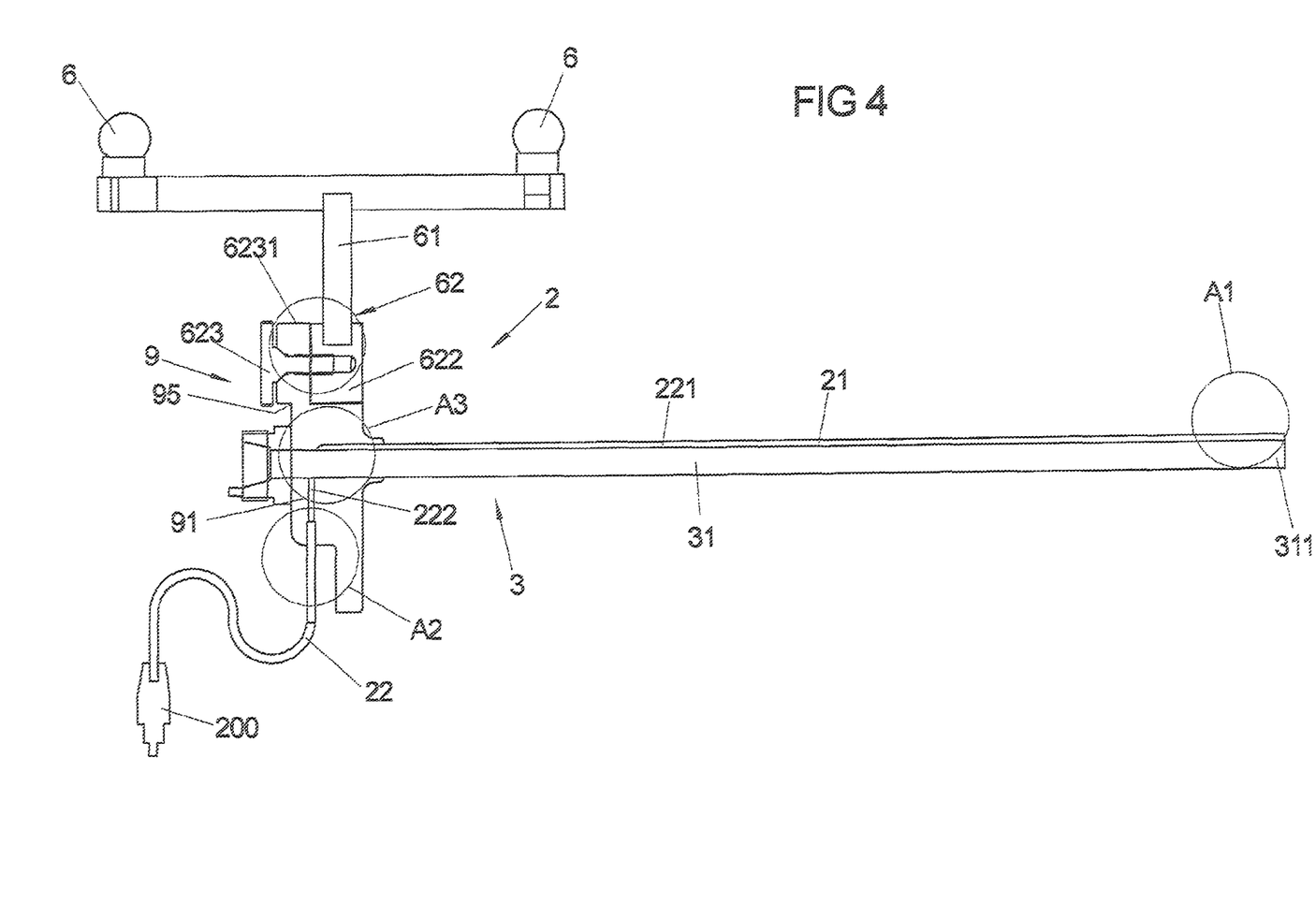
FIG. 4 shows a distance determining device according to the invention equipped for attachment to an endoscope.

FIG. 4 shows a distance determining device 2 according to an invention, which is arranged on an endoscope 3. The endoscope and the distance determining device of FIGS. 1 and 2 corresponds for instance to the arrangement of FIG. 4.

The distance determining device 2 comprise a channel designed in form of a tube 21 extending along an optical axis of the endoscope 3 in which a first section 221 of the light conducting fibre 22 extends. The optical axis of the endoscope 3 is determined in particular by the course of the shaft 31 (light conducting shaft) of the endoscope in which the imaged system thereof is located. The tube 21 with the light conducting fibre 22 extends along the shaft 31 such that it rests against an outer side of the (in particular rigid) shaft 31.

The distance determining device 2 comprises furthermore a base body 9 (e.g. made of a metal or a plastic), which forms a second channel 91, in which a second section 222 of the light conducting fibre 22 continues and is bent in direction towards the tube 21. The base body 9 is illustrated enlarged in FIG. 8.

The light conducting fibre 22 is guided in the tube 21 to a tip 311 of the endoscope shaft 31. The other end of the light conducting fibre 22, which exits from the base body 9, can be coupled in particular via a plug 200 to a light source.

As already shown in FIGS. 1 and 2 marking spheres 6 for determining the spatial position of the endoscope 3 are arranged on the endoscope 3. The marking spheres 6 are connected via a retainer 61, which is coupled pivotably via connecting means 62 (coupling mechanism) to the base body 9 of the distance determining device 2. The coupling mechanism for pivotably connecting the marking spheres to the base body 9 is described in more detail further below in context to the FIGS. 12a to 12c.

Figure 5:
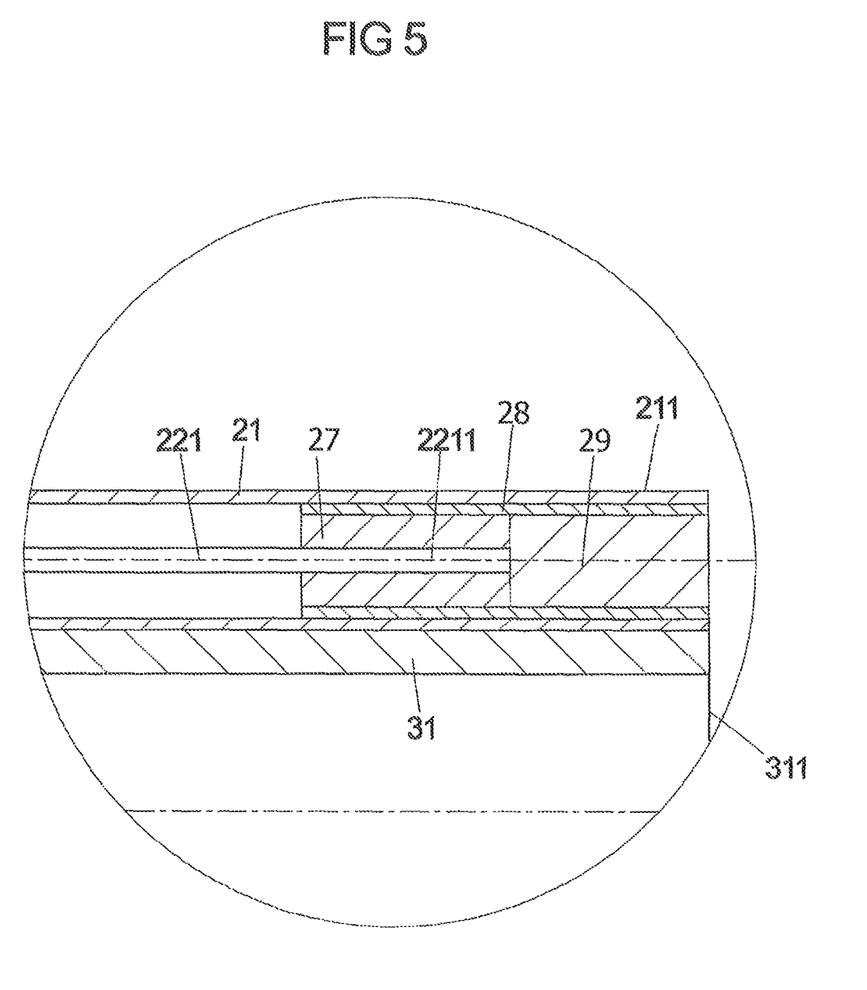
FIGS. 5 and 6 show sections of FIG. 4 in enlarged illustration.

FIG. 5 shows a section (indicated by the circle A1 in FIG. 5) of a front area (of the tip) of the distance determining device 2 with the section 221 of the light conducting fibre 22. It is recognizable that the tube 21 rests with a section of its outer side against the outer side of the also tube-like designed endoscope shaft 31. The end 2211 of the light conducting fibre 22 is attached (e.g. glued) in a capillary 27, which is inserted into the tube 21. The capillary 27 is again in a tulle 28, which comprises an outer diameter, which correspond approximately to the inner diameter of the tube 21, wherein the capillary 27 is glued into the tulle 28 and the tulle can again be attached (e.g. also glued) on the tube 21. The terms "capillary" and "tulle" are here hollow cylindrical structures, wherein the one (the "capillary") comprises a smaller diameter than the other (the "tulle"). The end 2211 of the light conducting fibre 21 is coupled to a rod lens 29, which is located between an end of the capillary 27 and a front side of an end 211 of the tube 21. The rod lens 29 is designed in particular in form of a gradient index lens.

Figure 6:
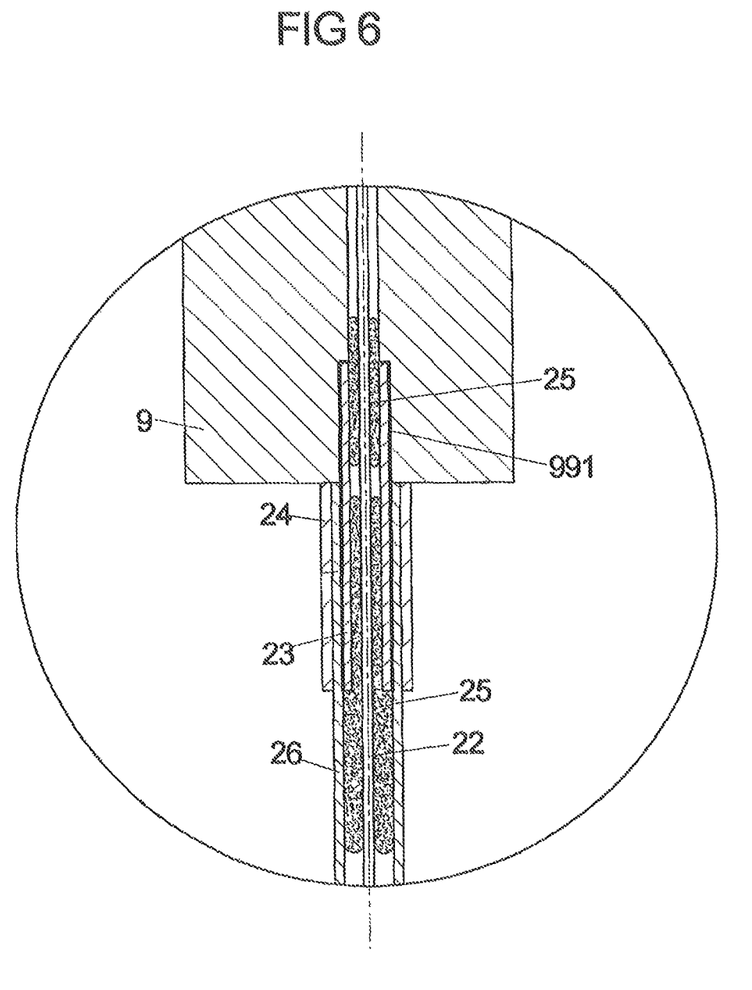

FIG. 6 shows a further section (section A2) of FIG. 4, particularly the connection of the light conducting fibre 22 to the base body 9 of the distance determining device 2. Accordingly, a subsection of the light conducting fibre is glued in an adapter tube 23 (by means of glue 25) and is additionally in particular crimped (via a crimp sleeve 24). The adapter tube 23 projects into a protective cover (protective tube 26), which encompasses the light conducting fibre 22.

The glue 25 fills out in particular a space between the light conducting fibre 22 and the protective tube 26 in order to realize a possible pressure-tight connection between the adapter tube and the light conducting fibre. Furthermore, an end of the adapter tube 23 projects into a hole 991 in the base body 9 and is fixed in this hole (in particular also glued). In order to achieve a possible pressure-tight connection also between the light conducting fibre and the base body 9 the glue is applied as even as possible on the glued surfaces.

Figure 7:
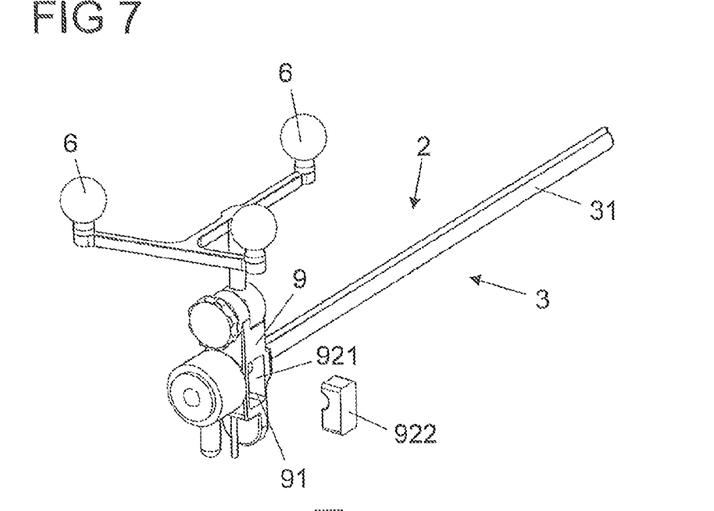
FIG. 7 shows a perspective view of the distance determining device of FIG. 4.

FIG. 7 shows a perspective illustration of the arrangement of FIG. 4. Hereby it is recognizable that the base body 9 comprises in the area of the second channel, through which the second section 222 of the light conducting fibre 22 extends, a notch 921, into which a guiding element 922 can be inserted. The side view of FIG. 8 of a section (in the area A3 of FIG. 4) shows that the guiding element 922 inserted into the notch 921.

Figure 8:
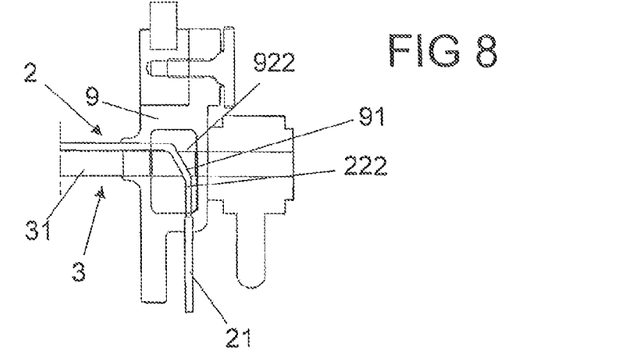
FIG. 8 shows a detailed view of the endoscope of FIG. 7.
Figure 9A:
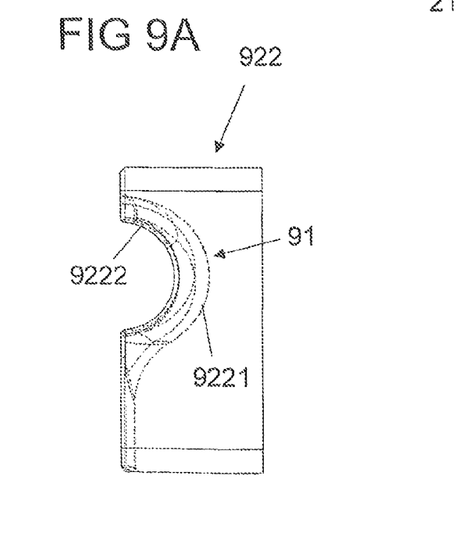
FIGS. 9A, 9B show different views of a part of the distance determining device of the endoscope of FIGS. 7 and 8.
Figure 9B:
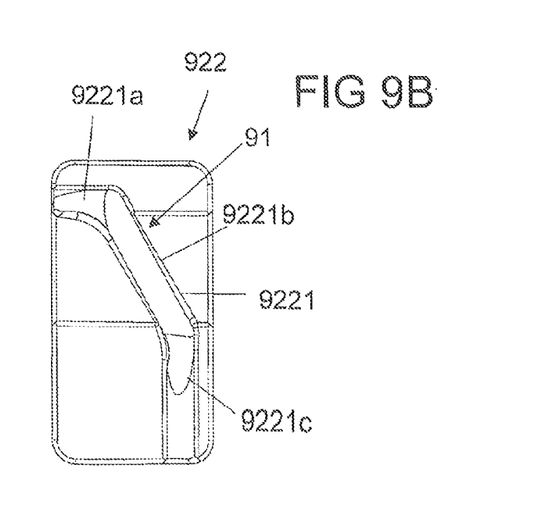

In the base body 9 (adjacent inside to the notch 921) as well as also in the guiding element 922 recesses are formed, respectively, which form together—if the guiding element 922 is inserted into the base body—the second channel for the light conducting fibre as well as a receptacle for the endoscope shaft. A recess formed in the base body 9 adjacent to the notch 921 (deepening, not illustrated) continues parallel to the shaft 31 and has a semi-circular cross section. Accordingly, the guiding element 922 comprises also recess 9222 with a semi-circular cross section, which is oriented along the shaft 31, if the guiding element 922 is inserted into the base body 9. Thus, the recess in the base body 9 and the recess 9222 in the guiding element 922 form after inserting the guiding element the passage opening through the base body 9, through which the endoscope shaft 31 extends to a further component of the endoscope (e.g. a camera or another optical or mechanical component).

Furthermore, a recess 9221 is formed in the guiding element 922, which together with a corresponding recess in the base body 9 (adjacent inside to the notch 921, i.e. in a bottom area of the notch 921) forms the second channel 91 for guiding the second section 222 of the light conducting fibre 22. The recess 9221 is likewise to the semicircular opening 9222 for the endoscope shaft 31 not in form of a passage opening, but is formed openly to one side of the guiding element such that the second channel is completed only by inserting the guiding element 922 into the base body. The inset 922 is connected in particular after insertion into the notch 921 to the base body 9 (in particular welded).

The second channel 91 resulting after the insertion of the inset 922 comprises in particular a first, second and third section such that the recess 9221 comprises in the guiding element 922 corresponding sections 9221a to 9221c. The second section 9221b (the middle section) is connected in each case via a curvature to the first or to the second section 9221a, 9221c such that although a light conducting fibre guided through the second channel can be bent by about 90°, the bending radius remains however as large as possible; for instance the first and the second curvature have a curvature radius of at least 5 mm.

Figure 10:
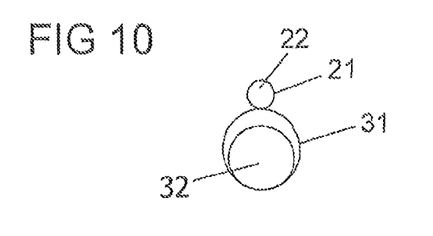
FIG. 10 shows a front view of the tip of the endoscope of FIGS. 7 and 8.

FIG. 10 shows a cross section of the endoscope shaft 31 of the endoscope 3 and the tube 21 arranged along the endoscope shaft 31, in which the section 221 of the light conducting fibre 22 of the distance determining device is guided. In the tube-like designed endoscope shaft 31 an image optic 32 (in particular in form of a rod lens) is arranged eccentrically relative to the centre point of the shaft 31. In the inner space of the shaft 31 which is not filled by the image optic 32 further light conducting fibres can extend via which light for illuminating an object to be displayed by means of the endoscope can be guided.

Tube 21 with the light conducting fibre 22 is arranged on a section of the outer side of the endoscope shaft 31, which comprises a preferably large distance from the axis of the image optic 32 (i.e. from the optical axis of the endoscope) so that a preferably large distance between the axis of the light conducting fibre and the optical axis of the endoscope is created since the accuracy of the distance measurement increases with a larger distance between these two axes.

Figures 11A, 11B:
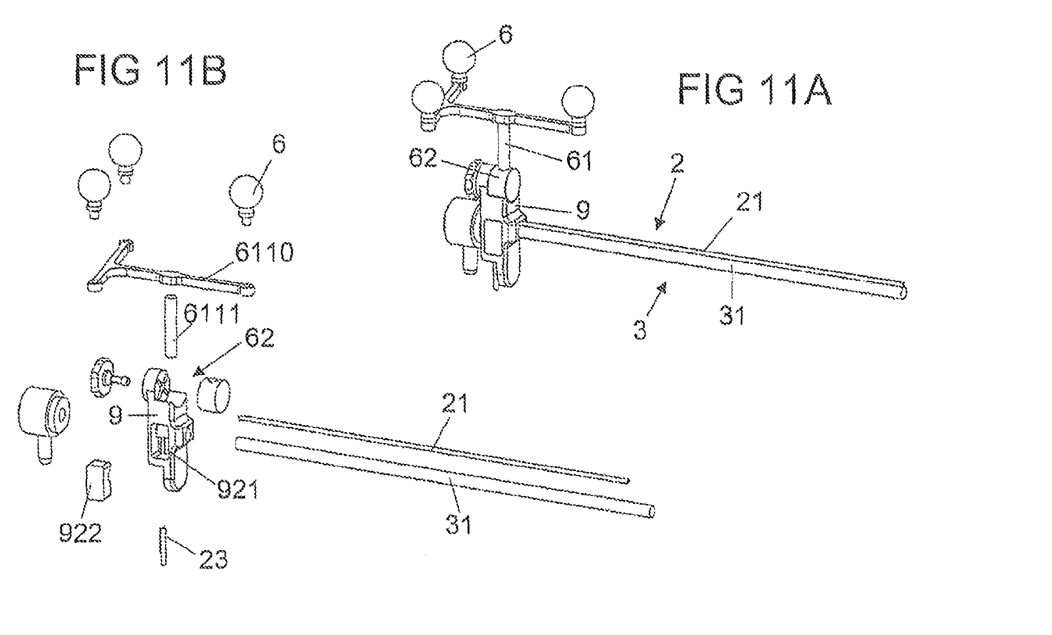

FIGS. 11A, 11B show the endoscope of FIGS. 4 and 7 in a perspective view (FIG. 11A) or explosive view (FIG. 11B).

Figure 12A:
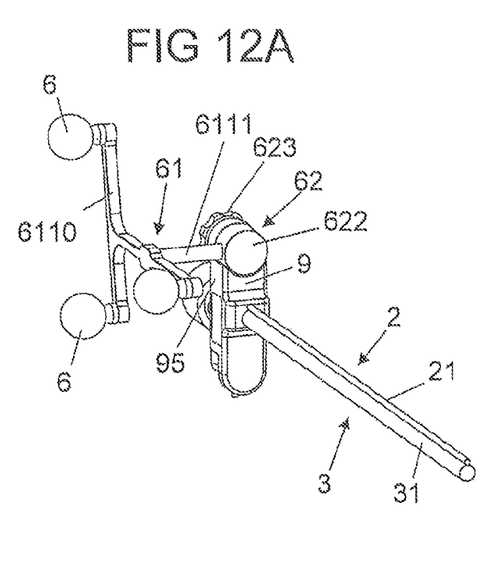
FIGS. 12A to 12C show the endoscope of FIGS. 7 and 8 for different pivot positions of the marking elements.
Figure 12B:
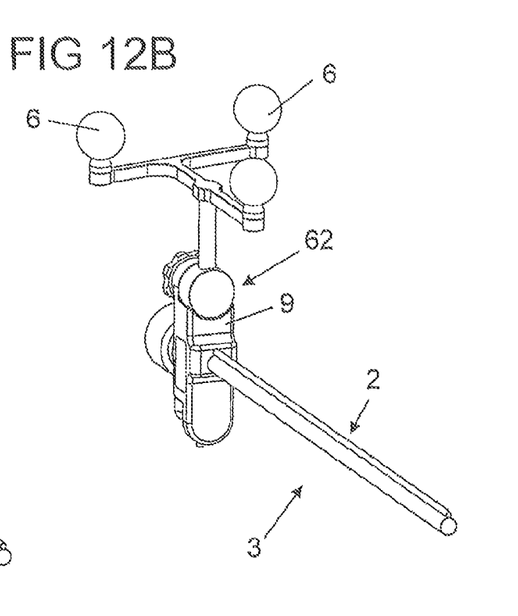
Figure 12C:
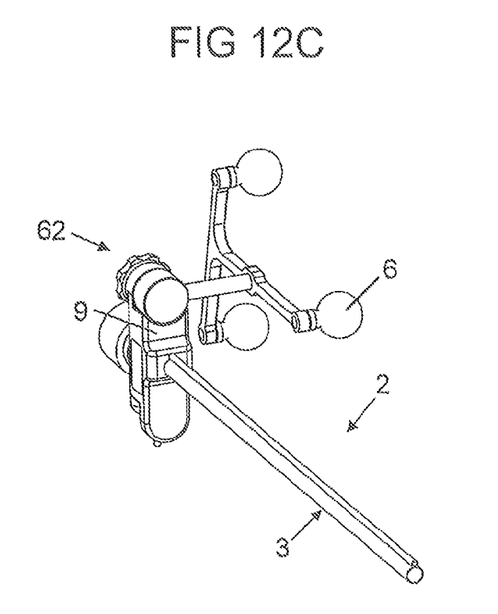

FIGS. 12A to 12C show in turn the endoscope of FIGS. 4 and 7 but for different positions of the marking spheres 6. As already mentioned before, the marking spheres 6 are connected via a retainer 61, which consists of a T-shaped first part 6110 and a rod-like second part 6111 extending vertical to this first part, to the base body 9 of the distance determining device.

The retainer 61 is connected via the second part 6111 to a joint of a pivoting mechanism 62 which allows a pivoting of the retainer 61 and thus an alignment of the marking spheres 6 relative to the base body 9. On the one hand, this has the purpose that the marking spheres 6 can be positioned such that they can be well detected by the measuring camera (compare FIGS. 1 and 2). On the other hand, the marking spheres can be brought in a reproducible manner in predefined positions. The marking spheres can be in particular positioned such that they hinder operating with the endoscope as less as possible. The position of the marking spheres can be determined when calibrating the endoscope (see above).

The pivoting mechanism 62 comprises a cylindrical element 622 on which the part 6111 of the retainer 61 is attached (on the lateral surface of the element 622). The cylindrical element 622 comprises on a front side (which faces away from the endoscope shaft 31) a thread into which a pin 6231 of a locking cap 623 is screwed (compare FIG. 4). Moreover, the locking cap 623 reaches through a hole in a wall element 95 of the base body 9 arranged between the locking cap and the cylindrical element such that the part 6111 and thus the marking sphere 6 are attached to the base body, but can be rotated along the axis of the pin 6231 of the locking cap if the locking cap is loosened. The pin 6231 continues in particular in direction of the optical axis (or the shaft 31) of the endoscope 3 such that the marking spheres 6 (i.e. the plane along which the marking spheres are arranged) can be rotated about an axis continuing parallel to the optical axis of the endoscope 3.

The invention claimed is:

1. A method for calibrating a distance determining device for determining a distance or a position vector between an optical system comprising an image optic and a camera and an object, comprising the steps,
    a) providing a detecting system, which comprises a plurality of marking elements, a measuring camera for detecting the spatial position of the marking elements, and means for projecting a light structure onto a calibration pattern;
    b) arranging the marking elements on the optical system and/or the distance determining device;
    c) providing a carrier to which calibration pattern is connected and/or which forms a calibration pattern;
    d) projecting a light structure onto the calibration pattern or the carrier forming the calibration pattern;
    e) detecting the marking elements, the calibration pattern and/or carrier marking elements arranged on the carrier by means of the measuring camera;
    f) detecting the light structure on the calibration pattern using the image optic and camera of the optical system;
    g) determining the spatial position of the marking elements and thus of the optical system using data of the measuring camera;
    h) determining coordinates of the calibration pattern in a first coordinate system associated with the measuring camera using data of the measuring camera;
    i) determining coordinates of an image of the light structure onto the calibration pattern in a second coordinate system associated with the image plane of the camera of the optical system; and
    j) calibrating the distance determining device using the determined coordinates of both coordinate systems and the determined spatial position of the optical system.

2. The method according to claim 1, wherein
    the optical system is in a first position relative to the carrier with the calibration pattern during the steps d)-i), the optical system is brought from the first into a second position relative to the carrier after carrying out the steps d)-i) and the steps d)-i) are carried out again, wherein
    first coordinates of the calibration pattern in the first coordinate system and second coordinates of the image of the calibration pattern and the light structure in the second coordinate system are determined for the first and the second position of the optical system, respectively, and a distance determining device is calibrated by means of these coordinates considering the respective determined spatial position of the optical system.

3. The method according to claim 2, wherein the calibration according to step j) comprises determining the first coordinates by means of the first and second coordinates of the calibration pattern and the second coordinates of the light structure, wherein particularly a proximity image adapted to the first and second coordinates of the calibration pattern is determined with which coordinates of the second coordinate system can be imaged in coordinates in the second coordinate system wherein the first coordinates of the light structure are determined using the proximity image on the second coordinates of the light structure.

4. The method according to claim 3, wherein the calibration pattern comprises multiple structures distanced to each other, wherein
    the first and the second coordinates of the structure of the calibration pattern are determined, respectively,
    the second coordinates of the light structure are determined; and
    the first coordinates of the light structure are determined using the second coordinates of the light structure and by interpolation of the first coordinates of the structure of the calibration pattern.

5. The method according to claim 3, wherein the calibration according to step j) comprises the generation of a calibration table in which the determined first and second coordinates of the light structure are contrasted with the first and the second position of the optical system, respectively.

6. The method according to claim 3, characterized in that wherein the first coordinates of the light structure are illustrated by a first proximity function and/or the second coordinates of the light structure are illustrated by a second proximity function for the different positions of the optical system, wherein particularly a transfer function for imaging the first proximity function onto the second proximity function is determined, wherein the first coordinates of the light structure can be determined from the second coordinates of the light structure by means of this transfer function.

7. The method according to claim 5, wherein the first and/or the second proximity function is determined in form of a line or a polynomial.

8. The method according to claim 5, wherein the first proximity function is determined and the optical system is brought into at least one further position, wherein the calibration according to step j) for the at least one further position comprises the following steps:
    i. determining the second coordinates of the light structure,
    ii. determining a line in the first coordinate system which continues through the position of the light structure in the image plane of the optical system and through an optical center of the optical system, and
    iii. determining the first coordinates of the light structure by determining the coordinates of the intersection point of the line with the first proximity function.

9. The method according to claim 1, wherein the first proximity function can be illustrated as a line and the first coordinates of a light structure can be determined in the first coordinate system by determining the coordinates of the intersection point of the line determined according to step ii) by the line illustrating the first proximity function or by determining the coordinates of a point of a common perpendicular relative to both lines.

10. The method according to claim 1, characterized in that wherein the calibration according to step j) comprises generating a calibration table in which the first coordinates of the light structure determined for the first and the second position as well as also the first coordinates of the light structure determined for the at least one further position of the optical system according to claim 1 are contrasted with to the respective second coordinates of the light structure.

11. The method according to claim 2, wherein by means of the determined coordinates of calibration pattern and the light structure and the determined spatial position of the optical system a position vector between a point of the light structure projected onto the carrier and a point of the optical system is determined for the first and the second position of the optical system, respectively, and the calibration according to step j) comprises the assigning of this position vector to the determined second coordinates of the light structure.

12. The method according to claim 1, wherein determining the spatial position of the optical system by means of the marking elements comprises determining a position of a front side of the optical system, which when using the optical system for imaging an object is to be turned towards this object.

13. A calibrating device for calibrating a distance determining device for determining a distance or a position vector between an optical system comprising an image optic and a camera and an object, in particular for carrying out a method according to claim 1, comprising
   a) a carrier to which a calibration pattern is connected and/or which forms a calibration pattern;
   b) means for projecting a light structure onto the calibration pattern;
   c) a detection system which comprises a plurality of marking elements arranged on the optical system and/or the distance determining device and a measuring camera for detecting the spatial position of the marking elements and/or carrier marking elements arranged on the carrier;
   d) position determining means for determining the spatial position of the optical system by means of the data of the measuring camera and detecting means comprising the camera of the optical system for detecting the light structure onto the calibration pattern;
   e) coordinates determining means for determining coordinates of the calibration pattern in a first coordinate system associated to the measuring camera, of coordinates of an image of the calibration pattern and the light structure in a second coordinate system associated to the image plane of a camera of the optical system; as well as
   f) calibration means for calibrating the distance determining device by means of the determined coordinates and the determined spatial position of the optical system.

14. The calibration device according to claim 11, wherein the calibration pattern is glued to the carrier, printed and/or engraved into the carrier.

15. The calibration device according to claim 11, wherein the carrier comprises connecting means for connecting to the optical system.

16. The distance determining device according to claim 14, further comprising a base body in which a receptacle for a light guiding shaft of the optical system continuing along an optical axis of the optical system is formed, wherein the second channel is formed by the way of a notch in the base body.

17. The distance determining device according to claim 14, wherein the second channel comprises a first, second and third section, wherein the second section is connected with one end thereof via a first curvature to the first section and with the other end thereof via a second curvature to the third section, wherein particularly the curvature radius of the first and/or other second curvature is at least 5 mm.

18. The optical system according to claim 16, characterized in that wherein the marking elements are arranged on a common holder which is connected pivotably to the optical system via the connecting means and/or the marking elements are pivotable about an axis via the connecting means, which continues parallel to an optical axis of the optical system.

* * * * *